(12) United States Patent
Ohshima

(10) Patent No.: US 6,939,331 B2
(45) Date of Patent: Sep. 6, 2005

(54) WING-LIKE NEEDLE PROTECTOR

(75) Inventor: Hiroshi Ohshima, Adachi-ku (JP)

(73) Assignee: Kabushiki Kaisha Top, Tokyo (JP)

( * ) Notice: Subject to any disclaimer, the term of this patent is extended or adjusted under 35 U.S.C. 154(b) by 0 days.

(21) Appl. No.: 10/483,624

(22) PCT Filed: May 17, 2002

(86) PCT No.: PCT/JP02/04782

§ 371 (c)(1),
(2), (4) Date: Jan. 14, 2004

(87) PCT Pub. No.: WO03/008019

PCT Pub. Date: Jan. 30, 2003

(65) Prior Publication Data

US 2004/0186446 A1 Sep. 23, 2004

(30) Foreign Application Priority Data

Jul. 18, 2001 (JP) ........................................ 2001-218476

(51) Int. Cl.[7] .................... A61M 5/00; A61M 5/178; A61M 5/32
(52) U.S. Cl. .................. 604/263; 604/164.08; 604/177; 604/110
(58) Field of Search ............................. 604/164.08, 110, 604/192, 198, 263, 174, 177; 128/919; 600/516

(56) References Cited

U.S. PATENT DOCUMENTS

| | | | | |
|---|---|---|---|---|
| 3,595,230 A | * | 7/1971 | Suyeoka et al. | ............ 604/192 |
| 4,627,843 A | | 12/1986 | Raines | |
| 4,631,058 A | | 12/1986 | Raines | |
| 4,820,282 A | * | 4/1989 | Hogan | ........................ 604/263 |
| 5,368,580 A | * | 11/1994 | Suzuki | ........................ 604/263 |
| 5,472,433 A | * | 12/1995 | Suzuki | ........................ 604/263 |
| 5,562,636 A | * | 10/1996 | Utterberg | ..................... 604/263 |
| 5,693,022 A | | 12/1997 | Haynes | |
| 2004/0102739 A1 | * | 5/2004 | Nakajima | ..................... 604/263 |

FOREIGN PATENT DOCUMENTS

| | | | |
|---|---|---|---|
| DE | 195 36 935 C1 | 2/1997 | |
| DE | 19536935 C1 | * 2/1997 | ............ A61M/5/32 |
| JP | 71047/1988 | 5/1988 | |
| JP | 1-317453 A | 12/1989 | |
| JP | 381577 A2 | 8/1990 | |
| JP | 2-239872 A | 9/1990 | |
| JP | 85043/1991 | 8/1991 | |
| JP | 3-275073 A | 12/1991 | |

* cited by examiner

Primary Examiner—Nicholas D. Lucchesi
Assistant Examiner—Catherine S. Williams
(74) Attorney, Agent, or Firm—Birch, Stewart, Kolasch & Birch, LLP

(57) ABSTRACT

There is here provided a wing-like needle protector which can surely prevent mistaken sticking, and can safely cap a hollow needle. The wing-like needle protector for housing a wing-like needle 1 which comprises a hollow needle 2, a holding cylinder 3 for holding a rear end of the hollow needle 2, and a pair of wing pieces 4, 4 formed integrally with the holding cylinder 3 so as to freely coalesce with each other. The protector comprises a gutter-shaped member 7 for housing the hollow needle 2, the holding cylinder 3 and the coalesced wing pieces 4, 4, and a gripper 8 protruded outward from a bottom surface of the gutter-shaped member 7. The gutter-shaped member 7 has a closed tip 9a of a portion 9 for housing the hollow needle 2, an opened rear end 10a of a portion 10 for housing the holding cylinder 3, and a narrowed area 7a where the holding cylinder 3 is fitted in a bottom portion, and the holding cylinder 3 is engaged with the narrowed area 7a. The narrowed area 7a may be partially provided on the bottom portion of the gutter-shaped member 7. The wing pieces 4, 4 of the gutter-shaped member 7 may be housed in and engaged with a portion 11 for housing the wing pieces 4, 4.

7 Claims, 3 Drawing Sheets

WING-LIKE NEEDLE PROTECTOR

TECHNICAL FIELD

The present invention relates to a protector for a wing-like needle used for insulin intramuscular injection.

BACKGROUND ART

As a needle used for medical practice such as insulin intramuscular injection, a wing-like needle has been known, which is provided with a hollow needle, and a pair of wing pieces formed integrally with a holding cylinder for holding a rear end of the hollow needle. The holding cylinder and the wing-like needle are made of soft resins, for example plasticized polyvinyl chloride.

In the case of using the wing-like needle, a medical practitioner such as a doctor or a nurse first removes a protector capping the hollow needle, mutually coalesces and holds the pair of wing pieces made of the soft resins, and then sticks the hollow needle into a muscle of an abdomen or the like of a patient. Then, the practitioner opens the pair of wing pieces left and right of the holding cylinder, and fastens them to the abdomen or the like of the patient by adhesive tape, thereby securing the hollow needle during the intramuscular injection.

After the end of the intramuscular injection, the wing-like needle is removed from the body of the patient, and discarded. However, if the hollow needle is exposed in this case, the medical practitioner or a person who discards the needle may stick the hollow needle into his finger or the like by mistake (simply referred to as mistaken sticking, hereinafter). Here, if the patient suffers from infectious disease such as HIV or acute hepatitis, the medical practitioner or the person who discards the needle is in danger of being infected with the disease through the hollow needle.

Conventionally, therefore, in order to prevent the mistaken sticking, the used hollow needle has been capped again with the protector removed before the use (recapping). The conventional protector is a hollow cylindrical body, which has a length equivalent to that of the hollow needle. The recapping is carried out by bringing the protector and the hollow needle close to each other in an extended direction of the hollow needle, and inserting the hollow needle from its tip into an opening end of the protector.

However, the protector is disadvantageous in that as fingers holding the protector are positioned in a moving direction of the tip of the hollow needle, the tip of the hollow needle may be mistakenly stuck into the fingers during the recapping.

DISCLOSURE OF THE INVENTION

An object of the present invention is to provide a wing-like needle protector, which can solve the foregoing disadvantage, surely prevent mistaken sticking, and safely cap a hollow needle.

In order to achieve the foregoing object, the present invention is characterized by a wing-like needle protector for housing a wing-like needle which comprises a hollow needle, a holding cylinder for holding a rear end of the hollow needle, and a pair of wing pieces formed integrally with the holding cylinder so as to freely coalesce with each other, wherein the protector comprises a gutter-shaped member including a portion for housing the hollow needle, a portion for housing the holding cylinder a portion for housing the coalesced wing pieces extended upward of the portion for housing the holding cylinder, and a gripper protruded outward from a bottom surface of the gutter-shaped member; the gutter-shaped member has a closed tip of the portion for housing the hollow needle, an opened rear end of the portion for housing the holding cylinder, and a narrowed area where a space between side walls of the gutter-shaped member is narrow so as to fit the holding cylinder in a bottom portion and the holding cylinder is engaged with the narrowed area, and the housed wing pieces are repulsively engaged with the portion for housing the wing pieces.

According to the first aspect of the present invention, the hollow needle and the holding cylinder of the wing-shape needle are housed in the gutter-shaped member while the wing pieces coalesce with each other. Thus, a medical practitioner such as a doctor or a nurse can draw out the wing-like needle from the protector by gripping the wing pieces housed in the coalescing state, and directly use the wing-like needle. Therefore, the medical practitioner can omit an operation of coalescing the pair of opened-out wing pieces for use.

For reattachment of the protector removed before the use to the used wing-like needle, the wing-like needle is gripped by one hand while the wing pieces coalesce with each other, and the gripper of the protector is gripped by the other hang. Then, by bringing the wing-like needle and the protector close to each other, the wing-like needle is housed in the gutter-shaped member. In this case, since the gripper of the protector is formed to be protruded outward from a bottom surface of the gutter-shaped member, the wing-like needle and the protector are moved in a direction intersecting an extended direction of the hollow needle. In such a case, fingers gripping the gripper of the protector are placed in positions shifted from an intended direction of a tip of the hollow needle during movement, and positioned on a backside of the gutter-shaped member to be protected by the same. Thus, according to the present invention, it is possible to surely prevent mistaken sticking of the tip of the hollow needle.

In addition, in the gutter-shaped member, since the tip of the portion for housing the hollow needle is closed, the tip of the hollow needle housed in the gutter-shaped member as described above is not protruded. Further, since the gutter-shaped member includes the narrowed area formed by narrowing the space between the side walls of the gutter-shaped member so as to be fitted in the bottom portion, when the wing-like needle is housed in the gutter-shaped member, the holding cylinder is fitted to the narrowed area, and engaged.

In this case, the holding cylinder is made flexible by its engagement with the narrowed area, applying a restoring force for return to an original shape. Thus, the holding cylinder is repulsively engaged with the narrowed area by the restoring force, making it possible to prevent falling-off of the wing-like needle from the gutter-shaped member.

In the wing-like protector of the present invention, the narrowed area needs not be provided on a full length of the bottom portion of the gutter-shaped member. If the narrowed area has a length, which provides an effect of preventing the falling-off of the wing-like needle from the gutter-shaped member, the narrowed area may be partially provided on the bottom portion of the gutter-shaped member.

In the wing-like needle, when the wing pieces are housed in the gutter-shaped member in a mutually coalescing state as described above, an opening-out force is applied. Thus, the wing pieces are repulsively engaged with the portion of the gutter-shaped member for housing the wing pieces by the opening-out force, making it possible to prevent falling-off of the wing-like needle from the gutter-shaped member.

When the wing-like needle is used for intramuscular injection of insulin or the like, the hollow needle is attached obliquely downward from the tip of the holding cylinder.

Thus, according to each aspect of the protector of the present invention, the gutter-shaped member is characterized in that the portion for housing the hollow needle is provided inclined from the portion for housing the holding cylinder toward the gripper. Therefore, since the gutter-shaped member is formed corresponding to shapes of the hollow needle and the holding cylinder of the wing-like needle, it is possible to attach the protector to the wing-like needle smoothly and easily.

Furthermore, according to each aspect of the protector of the present invention, the gripper is narrower than a width of the bottom surface of the gutter-shaped member. Thus, a step is formed between the gripper and the gutter-shaped member, and fingers gripping the gripper are hidden behind the gutter-shaped member and protected by the step. Therefore, it is possible to prevent the mistaken sticking more surely.

BEST MODE FOR CARRYING OUT THE INVENTION

Next, detailed description will be made of the preferred embodiments of the present invention with reference to the accompanying drawings.

Figure 1:
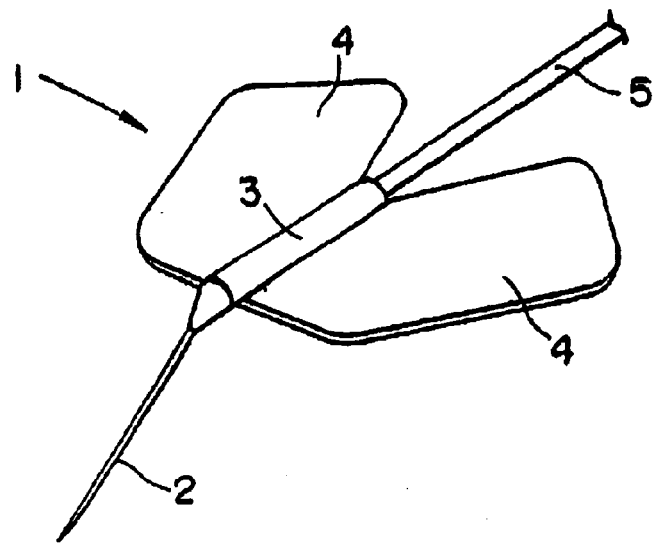
FIG. 1 is a perspective view showing an example of a wing-like needle according to the present invention.

As shown in FIG. 1, a wing-like needle 1 of an embodiment includes a hollow needle 2 having a sharp tip, a holding cylinder 3 for holding a rear end of the hollow needle 2, a pair of wing pieces 4 and 4 formed integrally with the holding cylinder 3 to be opened out, and a tube 5 attached to a rear end of the holding cylinder 3 to introduce drug solution into the hollow needle 2. The holding cylinder 3 and the wing pieces 4 and 4 are made of soft resins, for example, plasticized polyvinyl chloride (S-PVC), polyethylene (PE), and polypropylene (PP). The wing pieces 4 and 4 are elastically deformed, and freely coalesce with each other. The wing-like needle 1 is used for intramuscular injection of insulin or the like, and the hollow needle 2 is attached obliquely downward from a tip of the holding cylinder 3.

Figure 2:
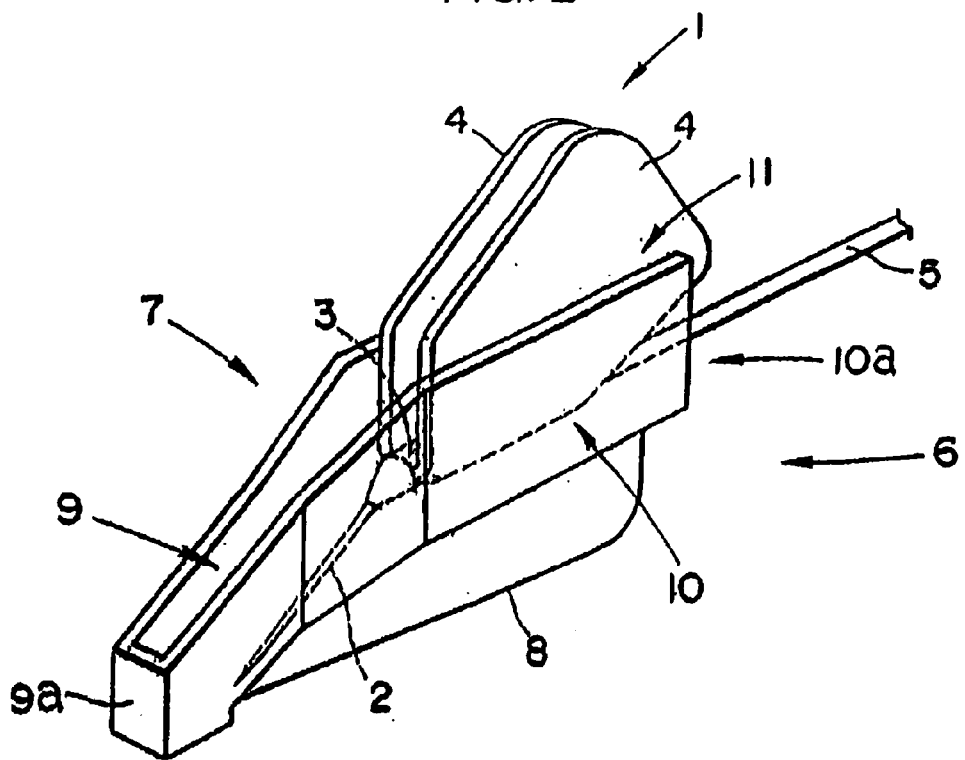
FIG. 2 is a perspective view showing an example of a wing-like needle protector according to the present invention.

On the other hand, as shown in FIG. 2, a protector 6 of an embodiment includes a gutter-shaped member 7 for housing the hollow needle 2, the holding cylinder 3 and the coalesced wing pieces 4, and a gripper 8 protruded outward from a bottom surface of the tub-shape member 7. In the gutter-shaped member 7, corresponding to the structure where the hollow needle 2 of the wing-shape needle 1 is attached obliquely downward from the tip of the holding cylinder 3, a portion 9 for housing the hollow needle 2 is inclined from a portion 10 for holding the cylinder 3 toward the gripper 8. A tip 9a of the portion 9 for housing the hollow needle 2 is closed to lock the hollow needle 2, thereby preventing its protrusion. A rear end 10a of the portion 10 for housing the holding cylinder 3 is opened to draw out the tube 5.

Figure 3:
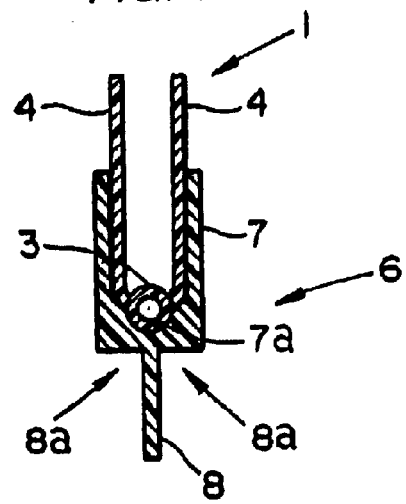
FIG. 3 is a sectional view taken on a line III—III of FIG. 2.
Figure 4:
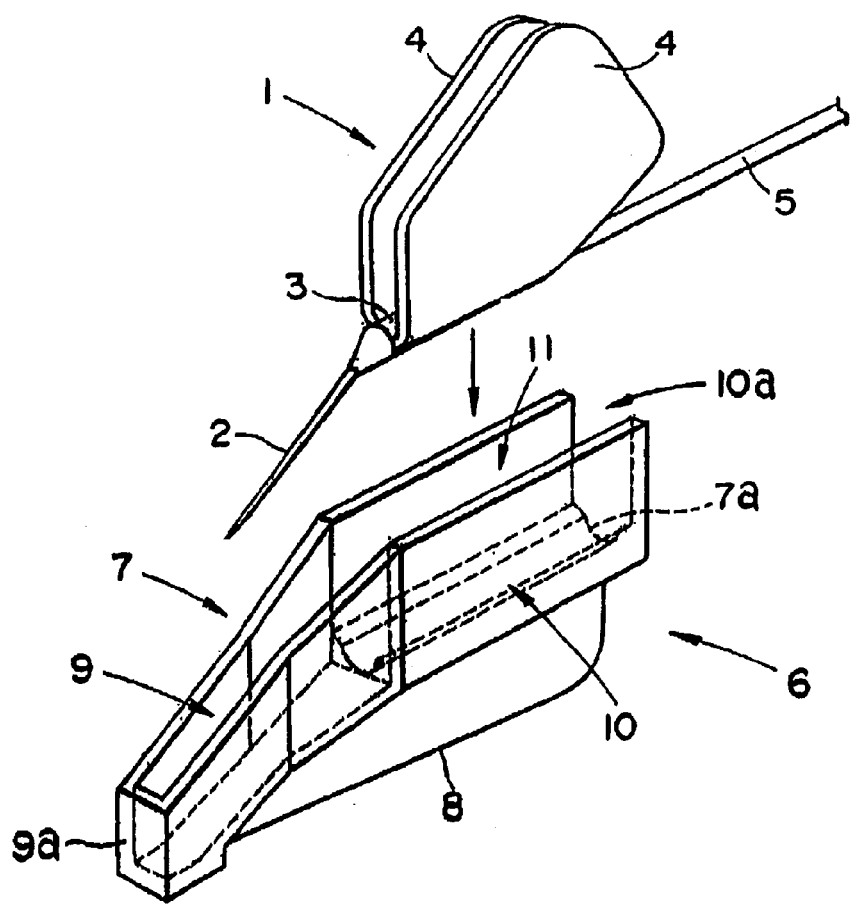
FIG. 4 is a perspective view showing a method of housing the wing-like needle in the wing-like needle protector shown in FIG. 2.

As shown in FIGS. 3 and 4, the gutter-shaped member 7 has a narrowed area 7a, in which a space between side walls of the gutter-shaped member 7 is narrowed to fit the holding cylinder 3 in a bottom portion. The narrowed area 7a is U-shaped in section, and formed to be slightly narrower than an outer diameter of the holding cylinder 3. The holding cylinder 3 that has been fitted to the narrowed area 7a and made flexible is repulsively engaged by a restoring force return to an original shape, thereby preventing falling-off of the wing-like needle 1 from the gutter-shaped member 7.

Further, above the portion 10 for housing the holding cylinder 3, a portion 11 is provided to house the wing pieces 4 and 4 are repulsively engaged with this portion 11 by their opening-out forces. The portion 11 for housing the wing pieces 4 and 4 needs not have a size to cover the entire wing pieces 4 and 4, in order to grip the wing pieces by fingers. It needs to have only a size for the foregoing repulsive engagement with the wing pieces 4 and 4 by the opening-out forces of the wing pieces 4 and 4.

On the other hand, as shown in FIG. 3, the gripper 8 is formed on the backside center of the bottom surface of the gutter-shaped member 7 to be narrow than the bottom surface. A step 8a is formed between the gripper 8 and the gutter-shaped member 7. Thus, the fingers gripping the gripper 8 are hidden behind the gutter-shaped member 7, and protected.

Preferably, the protector 6 of the embodiment is made of a hard resin, e.g., polypropylene (PP), acrylic nitrile butadiene-styrene copolymer resin (ABS) or polystyrene (PS), alternatively a semi-hard resin. As the protector 6 is made of such a resin, the narrowed area 7 can maintain the engagement with the holding cylinder 3 against the restoring force of the holding cylinder 3, or the portion 11 for housing the wing pieces 4 and 4 can maintain the engagement with wing pieces 4 and 4 against the their opening-out forces. Moreover, being made of the resin, the protector 6 can counter an external force when packaged. Not only blister packaging but also peel-open packaging are allowed.

According to the protector 6 of the embodiment, first, for use, in a state shown in FIG. 2, the wing pieces 4 and 4 exposed from the protector 6 are gripped by one hand, and the gripper 8 of the protector 6 is gripped by the other hand. Then, by moving these portions in directions away from each other, the wing-like needle 1 is drawn out from the protector 6. At this time, since the wing pieces 4 and 4 have coalesced with each other, the wing-like needle 1 can be put to immediate use after it is drawing out from the protector 6.

For reattachment of the protector 6 removed before the use to the wing-like needle 1 (recapping), the wing pieces 4 and 4 are gripped by one hand, and the gripper 8 of the protector 6 is gripped by the other hand. Then, as indicated by arrows in FIG. 3, the wing-like needle 1 and the protector 6 are moved such that the hollow needle 2 and the holding cylinder 3 are placed along an opening of the gutter-shaped member 7. In this case, since the wing-like needle 1 is moved in a direction intersecting an extended direction of the hollow needle 2, the fingers gripping the gripper 8 of the protector 6 are placed in positions shifted from an intended direction of the tip of the hollow needle 2. In addition, since the fingers gripping the gripper 8 are hidden behind the gutter-shaped member 7 by the step 8a as described above, they are protected from the wing-like needle 1 approaching the protector 6 by the gutter-shaped member 7.

Thus, according to the protector 6, it is possible to surely prevent mistaken sticking of the tip of the hollow needle 2 into the fingers gripping the gripper 8. Moreover, according to the protector 6, the holding cylinder 3 is repulsively engaged with the narrowed area 7a, and the wing pieces 4 and 4 are repulsively engaged with the portion 11 for housing the wing pieces 4 and 4. Thus, it is possible to surely prevent falling-off of the wing-like needle 1 that has been housed.

In the embodiment, the holding cylinder 3 is repulsively engaged with the narrowed area 7a, and the wing pieces 4 and 4 are repulsively engaged with the portion 11 for housing the wing pieces 4 and 4. However, a constitution may be employed, where only the narrowed area 7a repulsively engaged by the holding cylinder 3 is provided, the portion 11 for housing the wing pieces 4 and 4 is enlarged in width, and the wing pieces 4 and 4 are not repulsively engaged with this portion 11. As described above, when the portion 11 for housing the wing pieces 4 and 4 is enlarged in width, the holding cylinder 3 can be easily inserted by using this portion 11 as a guide for the holding cylinder 3.

As a constitution where the wing pieces 4 and 4 are repulsively engaged with the portion 11, the narrowed area 7a repulsively engaged by the holding cylinder 3 may not be provided.

Figure 5A:
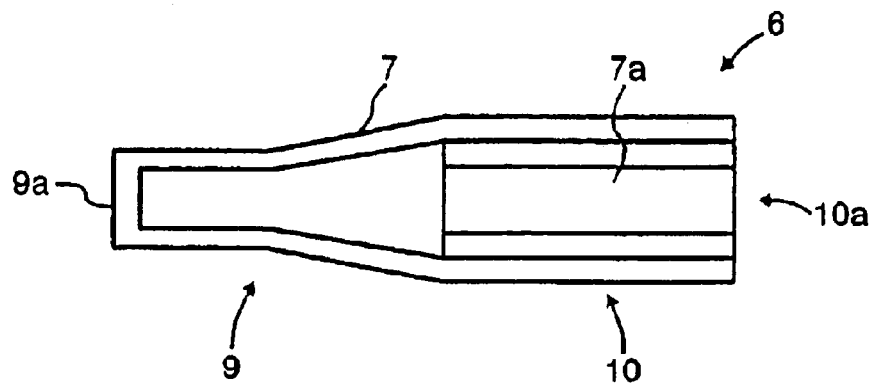
FIGS. 5(a) to 5(b) are plan views of the wing-like needle protector shown in FIG. 2.
Figure 5B:
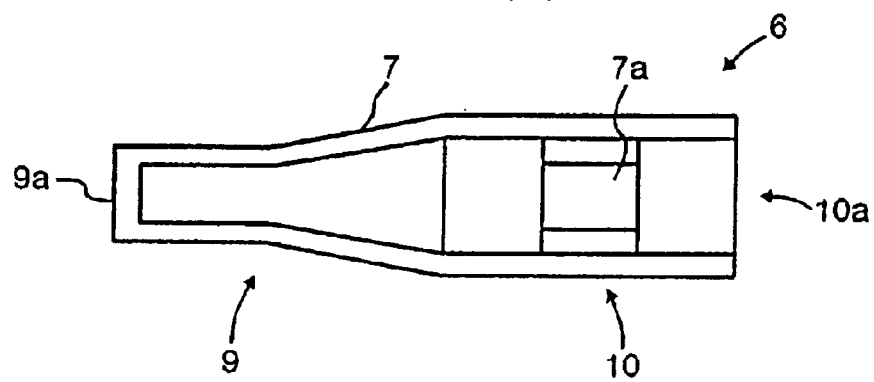
Figure 5C:
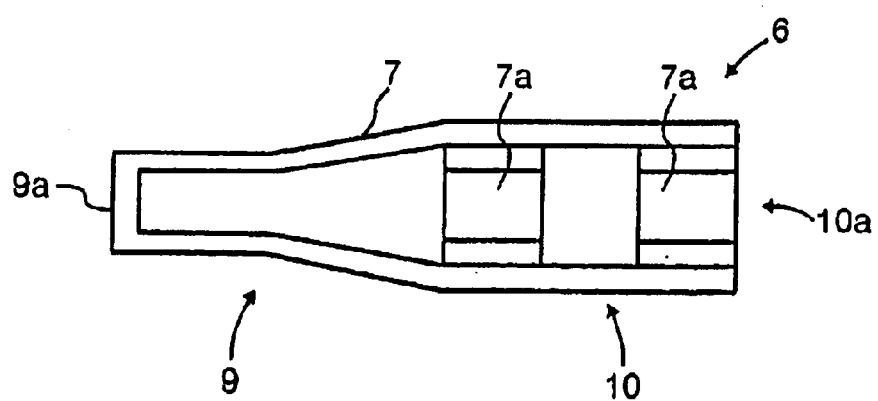

In the embodiment, as shown in FIG. 5(*a*), the narrowed area 7a is provided on a full length of the bottom surface of the gutter-shaped member 7. However, the narrowed area 7a only needs to have a length, which provides an effect of maintaining the engagement with the holding cylinder 3, and prevents falling-off of the wing-like needle 1. It may be provided partially on the bottom portion of the gutter-shaped member 7. If the narrowed area 7a is partially provided on the bottom portion of the gutter-shaped member 7, it may be provided in only one place on the bottom portion of the gutter-shaped member 7 as shown in FIG. 5(*b*). Alternatively, narrowed areas 7a may be provided in a plurality of places as shown in FIG. 5(*c*).

If the narrowed area 7a is provided partially on the bottom portion of the gutter-shaped member 7, the narrowed area 7a may be formed by, for example providing a pair of protruded portions oppositely to each other, which are formed by protruding parts of side walls of the gutter-shaped member 7 inward.

Furthermore, the embodiment has been described with reference to the wing-shape needle 1, where the hollow needle 2 is attached obliquely downward from the tip of the holding cylinder 3 for use in intramuscular injection of insulin or the like. However, the wing-like needle 1 may be constructed in such a manner that the hollow needle 2 is horizontally attached to the tip of the holding cylinder 3. In this case, the protector 6 is formed in such a manner that the portion 9 for housing the hollow needle 2 is formed horizontally to the portion 10 for housing the holding cylinder 3.

INDUSTRIAL APPLICABILITY

The present invention can be used for the wing-like needle as a medical instrument or the like.

What is claimed is:

1. A wing-like needle protector in combination with a wing-like needle which comprises a hollow needle, a holding cylinder for holding a rear end of the hollow needle, and a pair of wing pieces formed integrally with the holding cylinder so as to freely coalesce with each other, comprising:

a gutter-shaped member including a portion for housing the hollow needle a portion for housing the holding cylinder and a portion for housing the coalesced wing pieces extending upwardly of the portion for housing the holding cylinder with the coalesced wing pieces being repulsively engaged with the portion for housing the coalesced wing pieces and protruding upwardly from an upper end of the gutter-shaped member; and a gripper projecting outwardly from a bottom surface of the gutter-shaped member;

wherein the gutter-shaped member has a closed tip of the portion for housing the hollow needle, an opened rear end of the portion for housing the holding cylinder, and a narrowed area where a space between side walls of the gutter-shaped member is narrow so as to fit the holding cylinder in a bottom portion with the holding cylinder being engaged with the narrowed area.

2. The wing-like needle protector in combination with a wing-like needle according to claim 1, wherein the narrowed area is partially provided on the bottom portion of the gutter-shaped member.

3. The wing-like needle protector in combination with a wing-like needle according to claim 1, wherein the portion for housing the hollow needle is inclined from the portion for housing the holding cylinder toward the gripper.

4. The wing-like needle protector in combination with a wing-like needle according to claim 1, wherein a width of the gripper is narrower than a width of the bottom surface of the gutter-shaped member.

5. The wing-like needle protector in combination with a wing-like needle according to claim 2, wherein the portion for housing the hollow needle is inclined from the portion for housing the holding cylinder toward the gripper.

6. The wing-like needle protector in combination with a wing-like needle according to claim 2, wherein a width of the gripper is narrower than a width of the bottom surface of the gutter-shaped member.

7. The wing-like needle protector in combination with a wing-like needle according to claim 3, wherein a width of the gripper is narrower than a width of the bottom surface of the gutter-shaped member.

* * * * *